United States Patent
Clark et al.

(10) Patent No.: US 10,210,688 B2
(45) Date of Patent: Feb. 19, 2019

(54) SYSTEM AND METHOD FOR PROVIDING SAFETY AND SECURITY OF VARIOUS MATERIALS

(71) Applicant: TWINERGISTICS SAFETY AND SECURITY, LLC, Woodbridge, VA (US)

(72) Inventors: David Allan Clark, Woodbridge, VA (US); Patricia Mary McGowan, Woodbridge, VA (US); Brigid Mary McGowan, Woodbridge, VA (US)

(73) Assignee: TWINERGISTICS SAFETY AND SECURITY, LLC, Woodbridge, VA (US)

( * ) Notice: Subject to any disclaimer, the term of this patent is extended or adjusted under 35 U.S.C. 154(b) by 0 days.

(21) Appl. No.: 15/791,861

(22) Filed: Oct. 24, 2017

(65) Prior Publication Data

US 2018/0197360 A1      Jul. 12, 2018

Related U.S. Application Data

(60) Provisional application No. 62/444,916, filed on Jan. 11, 2017.

(51) Int. Cl.
*G07F 13/06* (2006.01)
*G06Q 20/18* (2012.01)
(Continued)

(52) U.S. Cl.
CPC ............ *G07C 9/00309* (2013.01); *A45F 3/16* (2013.01); *A47G 23/16* (2013.01); *G05B 15/02* (2013.01);
(Continued)

(58) Field of Classification Search
CPC .......... G07C 2009/00357; G07C 2009/00412; G07C 2009/00793; G07C 9/00309;
(Continued)

(56) References Cited

U.S. PATENT DOCUMENTS

| | | | | |
|---|---|---|---|---|
| 9,245,403 B2* | 1/2016 | Geigel | ..................... | G07F 9/026 |
| 2016/0089303 A1* | 3/2016 | Latorraca | ................ | G07F 11/62 |
| | | | | 312/209 |

(Continued)

*Primary Examiner* — Dionne H Pendleton
(74) *Attorney, Agent, or Firm* — Carlos R. Villamar; The Villamar Firm PLLC

(57) ABSTRACT

A system, method and computer program product for providing safety and security of materials, including an onsite measuring device configured to measure dispensed liquid, fluids, or materials from a container, and transmit measurement information; a base station device configured to receive the transmitted measurement information, and transmit the received measurement information over a communications network; a server device configured to receive and process the measurement information, and transmit an authorization over the communications network to dispense the liquid, fluids, or materials in the container based on the processed measurement information; a mobile device configured to receive the authorization from the server device to lock or unlock the container so as to dispense the liquid, fluids, or materials in the container; and a locking device configured to lock or unlock the container to dispense the liquid, fluids, or materials based on the authorization received by the mobile device.

18 Claims, 5 Drawing Sheets

(51) Int. Cl.
- *G07C 9/00* (2006.01)
- *G05B 15/02* (2006.01)
- *A47G 23/16* (2006.01)
- *G07F 13/10* (2006.01)
- *G07F 11/00* (2006.01)
- *G16H 20/13* (2018.01)
- *A45F 3/16* (2006.01)
- *G08C 17/02* (2006.01)
- *H04W 12/08* (2009.01)

(52) U.S. Cl.
CPC ........ *G07C 9/00896* (2013.01); *G07F 11/002* (2013.01); *G07F 13/10* (2013.01); *G16H 20/13* (2018.01); G07C 2009/00357 (2013.01); G07C 2009/00412 (2013.01); G07C 2009/00793 (2013.01); G08C 17/02 (2013.01); H04W 12/08 (2013.01)

(58) Field of Classification Search
CPC ... G07C 9/00896; G08C 17/02; H04W 12/08; H04W 4/80; A45F 3/16; A47G 19/2227; A47G 2019/2238; A47G 23/16; G01F 1/075; G01F 23/00; G01F 23/0076; G01F 23/263; G01F 23/265; G01F 23/2845; G01F 23/2921; G01F 23/296; G01F 23/74; G01F 25/0061; G05B 15/02; G06Q 20/102; G06Q 20/18; G06Q 20/3224; G06Q 20/3278; G06Q 20/401; G06Q 20/4014; G07F 11/002; G07F 13/02; G07F 13/025; G07F 9/026

See application file for complete search history.

(56) References Cited

U.S. PATENT DOCUMENTS

| | | | |
|---|---|---|---|
| 2016/0196711 A1* | 7/2016 | Castellani | G07F 9/026 700/237 |
| 2017/0340147 A1* | 11/2017 | Hambrock | A47G 19/2227 |
| 2018/0257921 A1* | 9/2018 | Li | B67D 1/0888 |

* cited by examiner

SYSTEM AND METHOD FOR PROVIDING SAFETY AND SECURITY OF VARIOUS MATERIALS

CROSS REFERENCE TO RELATED DOCUMENTS

The present invention claims priority to U.S. Provisional Patent Application Ser. No. 62/444,916 of Clark et al., entitled "SYSTEM AND METHOD FOR PROVIDING SAFETY AND SECURITY OF VARIOUS MATERIALS," filed on 11 Jan. 2017, now pending, the entire disclosure of which is hereby incorporated by reference herein.

BACKGROUND OF THE INVENTION

Field of the Invention

The present invention generally relates to systems and methods for providing safety and security of objects, materials, and the like, and more particularly to a method and system for providing safety and security of objects, materials, and the like, including security solutions for measurements, materials, field areas, field devices, field operations, and the like, of industries, for example, including industries related to liquids, chemicals, gases, equipment, and various other substances, and the like, including non-hazardous and hazardous material, and providing security via alerts, and the like, tracking, mobile apps, and devices related thereto, and the like.

Discussion of the Background

In recent years, systems and methods for providing safety and security of objects, materials, and the like, have been developed. However, such systems and methods often are not robust with respect to security solutions for measurements, materials, field areas, field devices, field operations, and the like, of industries, for example, including industries related to liquids, chemicals, gases, equipment, and various other substances, and the like, including non-hazardous and hazardous material, and the like.

SUMMARY OF THE INVENTION

Therefore, there is a need for methods and systems that address the above and other problems with systems and methods for providing safety and security of objects, materials, and the like. Accordingly, the above and other needs are addressed by the illustrative embodiments of the present invention, which provide a novel method and system for providing safety and security of objects, materials, and the like, including security solutions for measurements, materials, field areas, field devices, field operations, and the like, of industries, for example, including industries related to liquids, chemicals, gases, equipment, and various other substances, and the like, including non-hazardous and hazardous material, and providing security via alerts, and the like, tracking, mobile apps, and devices related thereto, and the like. For example, the problems of security and safety of substances are addressed by the illustrative embodiments of the present invention, which provides the security and safety of the entire operation of substances not secured, which include a suite of various solutions to increase safety and to implement a set of security devices to secure equipment, materials, substance, data, and the like, through various industries and at a reasonable cost.

Accordingly, in an illustrative aspect, there is provided a system, method and computer program product for providing safety and security of materials, including an onsite measuring device configured to measure dispensed liquid, fluids, or materials from a container, and transmit measurement information; a base station device configured to receive the transmitted measurement information, and transmit the received measurement information over a communications network; a server device configured to receive and process the measurement information, and transmit an authorization over the communications network to dispense the liquid, fluids, or materials in the container based on the processed measurement information; a mobile device configured to receive the authorization from the server device to lock or unlock the container so as to dispense the liquid, fluids, or materials in the container; and a locking device configured to lock or unlock the container to dispense the liquid, fluids, or materials based on the authorization received by the mobile device.

The locking device is configured to lock or unlock the container to dispense the liquid, fluids, or materials in the container based on near field data (NFD) encryption communications with the mobile device, and the authorization received by the mobile device.

The server is configured to generate for display logistical information based on the received and processed measurement information, including hierarchical event monitoring and analysis within an enterprise network including deploying a plurality of network monitors in the enterprise network.

The onsite measuring device is configured to measure the liquid, fluids, or materials in the container based on volume inside the container for providing a digital representation or display thereof.

The locking device is configured to employ an encryption based locking and unlocking mechanism for tracking, and securing the liquid, fluids, or materials in the container, and for providing corresponding information to the server.

The server device is configured to send and receive information regarding measurements, locking and unlocking detection during collection and movement of the liquid, fluids, or materials in the container, and provide the received information to a computer system of an end-user customer.

Still other aspects, features, and advantages of the present invention are readily apparent from the following detailed description, simply by illustrating a number of illustrative embodiments and implementations, including the best mode contemplated for carrying out the present invention. The present invention also is capable of other and different embodiments, and its several details can be modified in various respects, all without departing from the spirit and scope of the present invention. Accordingly, the drawings and descriptions are to be regarded as illustrative in nature, and not as restrictive.

BRIEF DESCRIPTION OF THE DRAWINGS

The embodiments of the present invention are illustrated by way of example, and not by way of limitation, in the figures of the accompanying drawings, in which like reference numerals refer to similar elements, and in which:

FIG. 1 is an illustrative field safety and security system and method for safety and security of liquid usage, and the like;

FIG. 5 is a real-world application of the system and method of FIGS. 1-4, for example, as applied to an oil or grain industry, and the like.

DETAILED DESCRIPTION OF THE PREFERRED EMBODIMENTS

Figure 1:
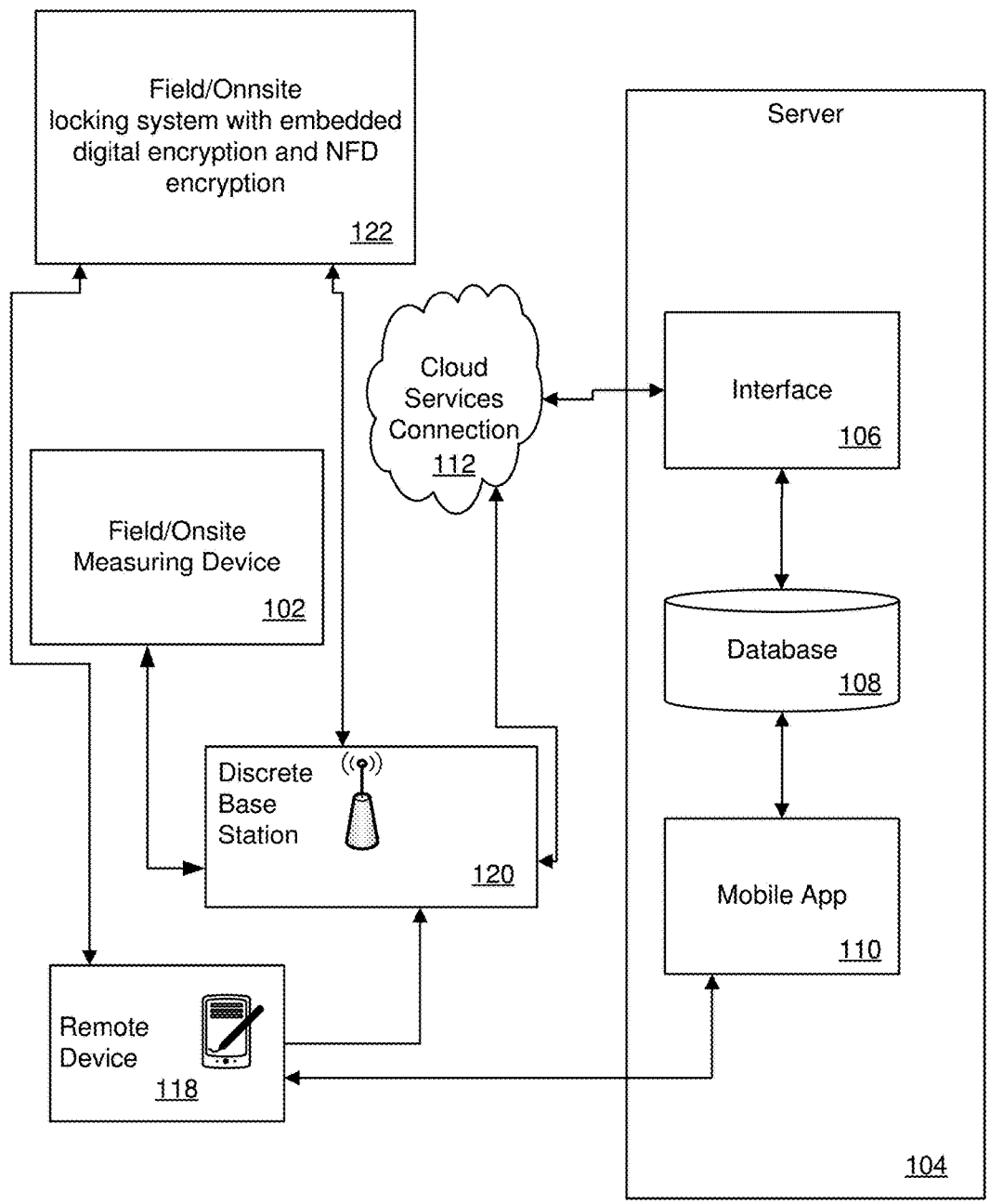

The present invention includes recognition that with the many changes over the years in environmental and political climate in technologies and various threats in many industries, the safety and security for various liquids, chemicals, gases, equipment, food, agriculture and various other substances, which includes non-hazardous and hazardous materials has become a major priority for both private business, public areas, governmental agencies, and the like. Such industries can include almost any business that must secure such various materials, and the like. However, the safety in measuring, transporting and securing or detecting such materials can take an extensive amount of time, processing and expense to those, who must address the challenges of safety and security.

The present invention includes recognition that the safety, the condition of being protected from or to cause danger, risk or injury, and security, the state of being free from danger or threat, for various liquids, chemicals, gases, equipment and various other substances is an enormous problem for many industries. For example, industries, such as oil industries, chemical industries, food and drug industries, agriculture industries, fossil fuels and materials industries, and the like, are affected by many of the above-noted problems with respect to the safety and security of materials, equipment, and the like.

There may exist various processes, hardware, software, and the like, developed for security and safety of various liquids, chemicals, gases, equipment, various other substances, and the like. However, the present invention includes recognition that most security and safety systems for the above-noted substances may be rare and very expensive. With the limited number of products and safety to secure such substances many workers are effected by gases, other risks, accidents on site, and the like. Accordingly, the present invention includes recognition that the security and safety of such workers, equipment, and product becomes a vital need for commercial companies, governments, and the like.

The present invention includes recognition that the world economy is going through massive disruption, and as humankind continues to be extremely dependent on organic sources of energy, foods, fluids, gases, and other forms of energy, not securing such substances can negatively affect such industries, locally and globally. In addition, new innovations have not flowed to such areas from upstream sectors to midstream infrastructure, refinery operations, chemical facilities, and various food and drugs, and the like. Further, the value from recent technologies have had very little impact in such areas, where the cost of expensive tools and devices have not made for more efficient operations as such costs are prohibitive, and with the measuring, and securing of such substances having had very little benefits to the application of such new technologies and innovations.

Accordingly, the present invention, for example, generally includes novel methods and systems, including field devices that can measure, track, add additional safety, and the like, for example, to isolated and remote fields, areas, and the like. Advantageously, such methods, systems and devices bring technology to areas that do not currently have such capabilities. In some cases, well-known structures and devices are shown in block diagram from in order to avoid unnecessarily obscuring the current invention.

Referring now to the drawings, wherein like reference numerals designate identical or corresponding parts throughout the several views and more particularly to FIG. 1 there is illustrated a field safety and security system and method 100 for safety and security of liquid usage, and the like. In FIG. 1, the system and method 100 can include various field devices configured to measure liquids, secure the fluids, and transmit the resulting data. For example, a field/onsite measuring device 102 (e.g., including various sensor devices, such as LiDAR measurement-based devices, sonar measurement-based devices, thermal/temperature measurement-based devices, laser measurement-based devices, displacement measurement-based devices, weight measurement-based devices, volume measurement-based devices, etc.) is provided and configured to measure liquid, fluids, materials, and the like, and dispensement thereof, and then transmit the measurement data to a discrete base station device 120. The discrete base station device 120 then transmits the received data, for example, via network communication over a cloud network 112, to a suitable interface 106 of a virtual cloud or server 104, which includes a database 108. The data can then be converted, analyzed, and the like, by the web server 104, which then transmits via mobile application 110 the processed data to web, client, and the like, mobile devices 118. A field/onsite locking system 122 is provided and configured with embedded digital encryption, near field device (NFD) encryption, and the like, and configured to lock and protect liquid, fluid, material, or any suitable material in the field, and the like, and once locked can only be opened via mobile NFD encryption, and the like. The various devices can communicate with the cloud services 112, the web application interface 106, the database 108, and the mobile application 110 and the remote device 118. Advantageously, the system and method 100 can store, report, calculate, and the like, various information available for analysis, reporting, and the like.

Figure 2:
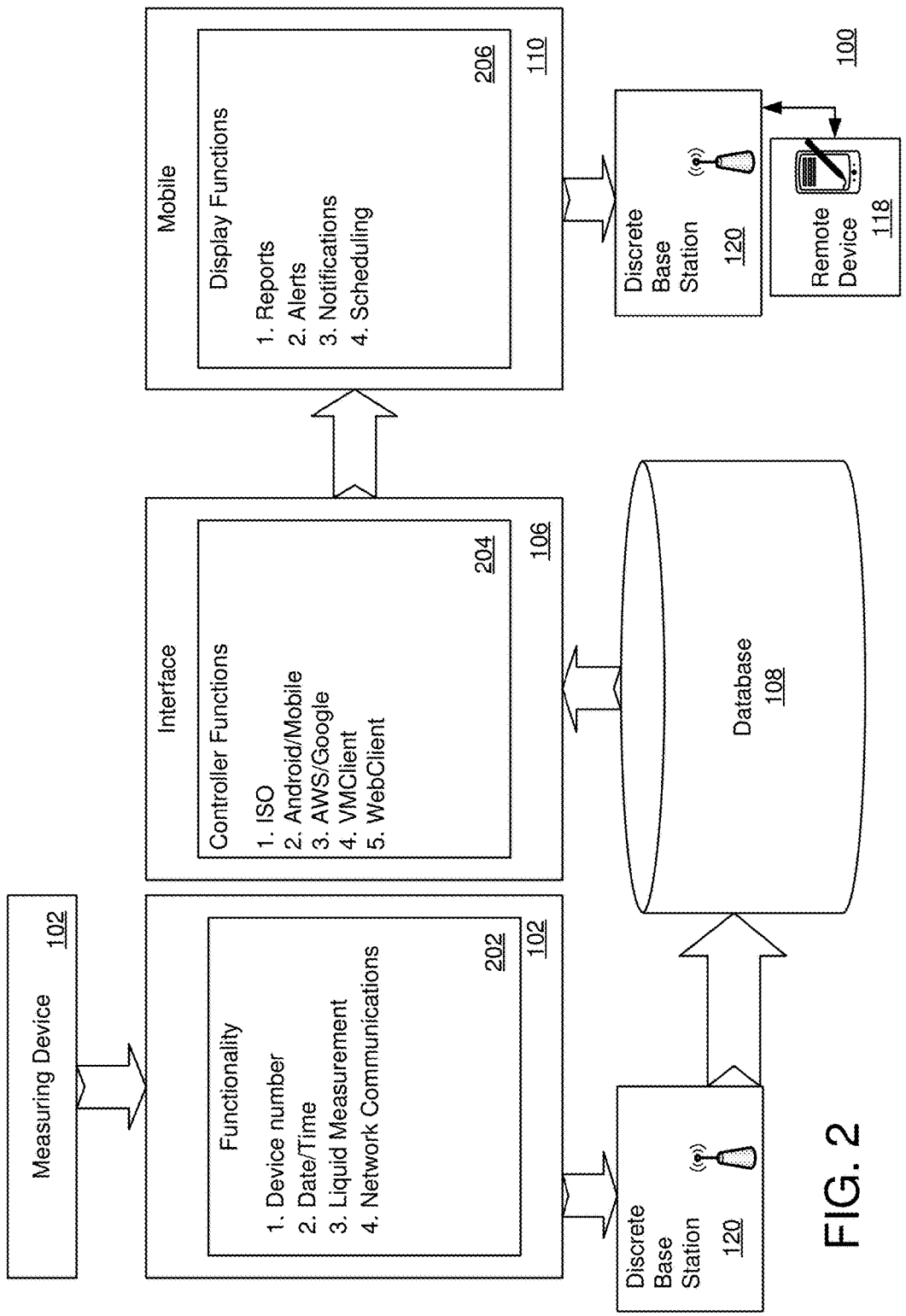
FIG. 2 is an illustrative measuring device for use with the system and method of FIG. 1.

FIG. 2 is an illustrative measuring device for use with the system and method of FIG. 1. In FIG. 2, the measuring device 102 is configured to generate detailed information 202, including measurements, readings, and the like, related to various liquids, materials, and the like, being monitored via network communication, and for example, including a device number, date/time of reading, liquids or solids measurement, and the like. The device 102 via the base station 120 then communicates the generated detailed information to the database 108 via the cloud services 112, and the web application interface 106. The web application interface 106 includes controller functions 204, for example including ISO functionality, Android/mobile functionality, Amazon Web Services (AWS)/Google functionality, VMClient functionality, WebClient functionality, and the like. The mobile application 110 then can perform various functions 206, for example, including storing, reporting, calculating, and the like, information available for analysis and reporting for generating reports, alerts, notifications, scheduling tasks, and the like, and which are then transmitted to the remote device 118 via the base station 120.

Figure 3:
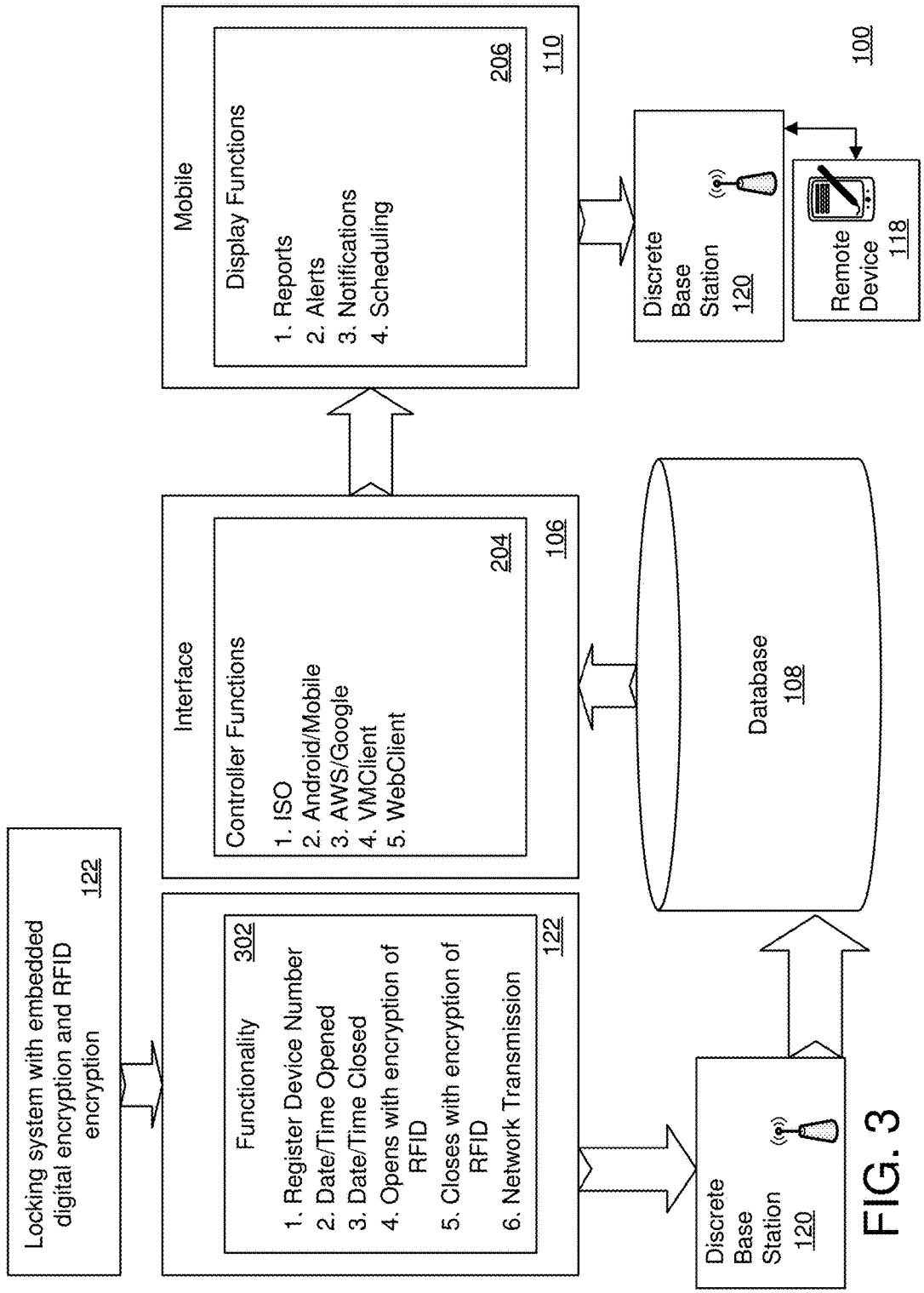
FIG. 3 is an illustrative locking system for use with the system and method of FIG. 1.

FIG. 3 is an illustrative locking system for use with the system and method of FIG. 1. In FIG. 3, the locking device 122 generates detailed information, readings, and the like, for example, including various locking/unlocking occurrences, tampering, monitoring date/time, system accountability with digital encryption data and Radio-frequency identification (RFID) encryption, and the like. For example, the device 122 can include functionality 302, including registering the device number, the date/time of reading, date/time opened/closed, opening/closing of the device 122 with RFID encryption, and network communications. The device 122 via the base station 120 then communicates the generated detailed information, readings, and the like, to the database 108 via the cloud services 112, and the web application interface 106, which performs the functionality as previously described with respect to FIGS. 1-2.

Figure 4:
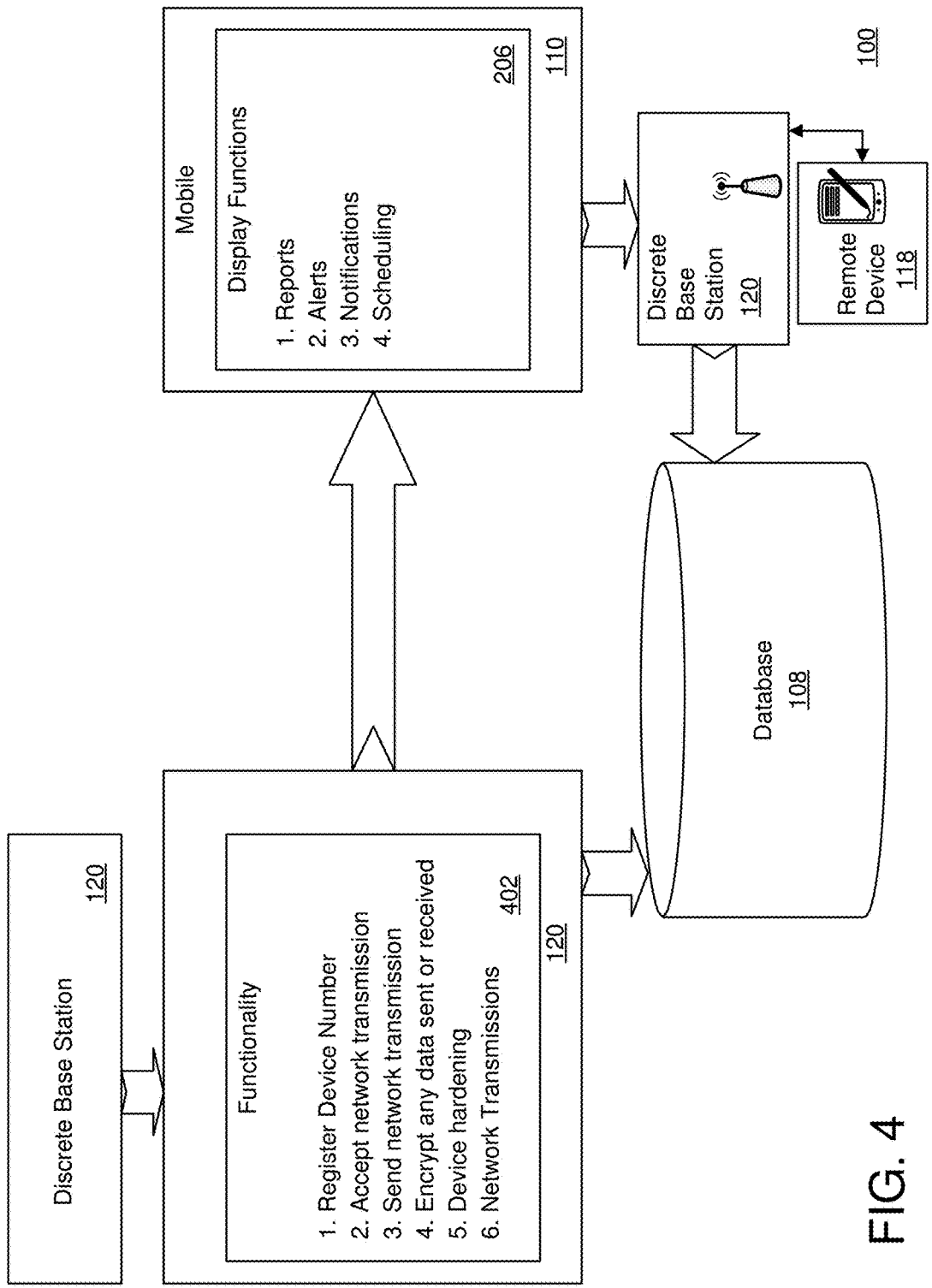
FIG. 4 is an illustration discrete base station for use with the system and method of FIG. 1.

FIG. 4 is an illustration discrete base station for use with the system and method of FIG. 1. In FIG. 4, the base station 120 is configured to communicate and transmit encrypted information and readings, for example, including the collected and generated data, information, and the like, as described with respect to FIGS. 1-3. For example, the device 120 can include functionality 402, including registering the device number, the date/time of readings, accepting, sending and receiving network transmissions, encrypting data sent or received, device hardening, and the like. The device 120 then communicates the received or generated information, and the like, with the database 108 via the cloud services 112, and the web application interface 106, and with the mobile application 110, which perform the functionality as previously described with respect to FIGS. 1-3. Advantageously, data received, generated, transmitted, and the like, can be encrypted. The device 120 is also configured to be hardened for communication use with the cloud services 112, the web app 106, the database 108, and the devices 110 and 118.

Figure 5:
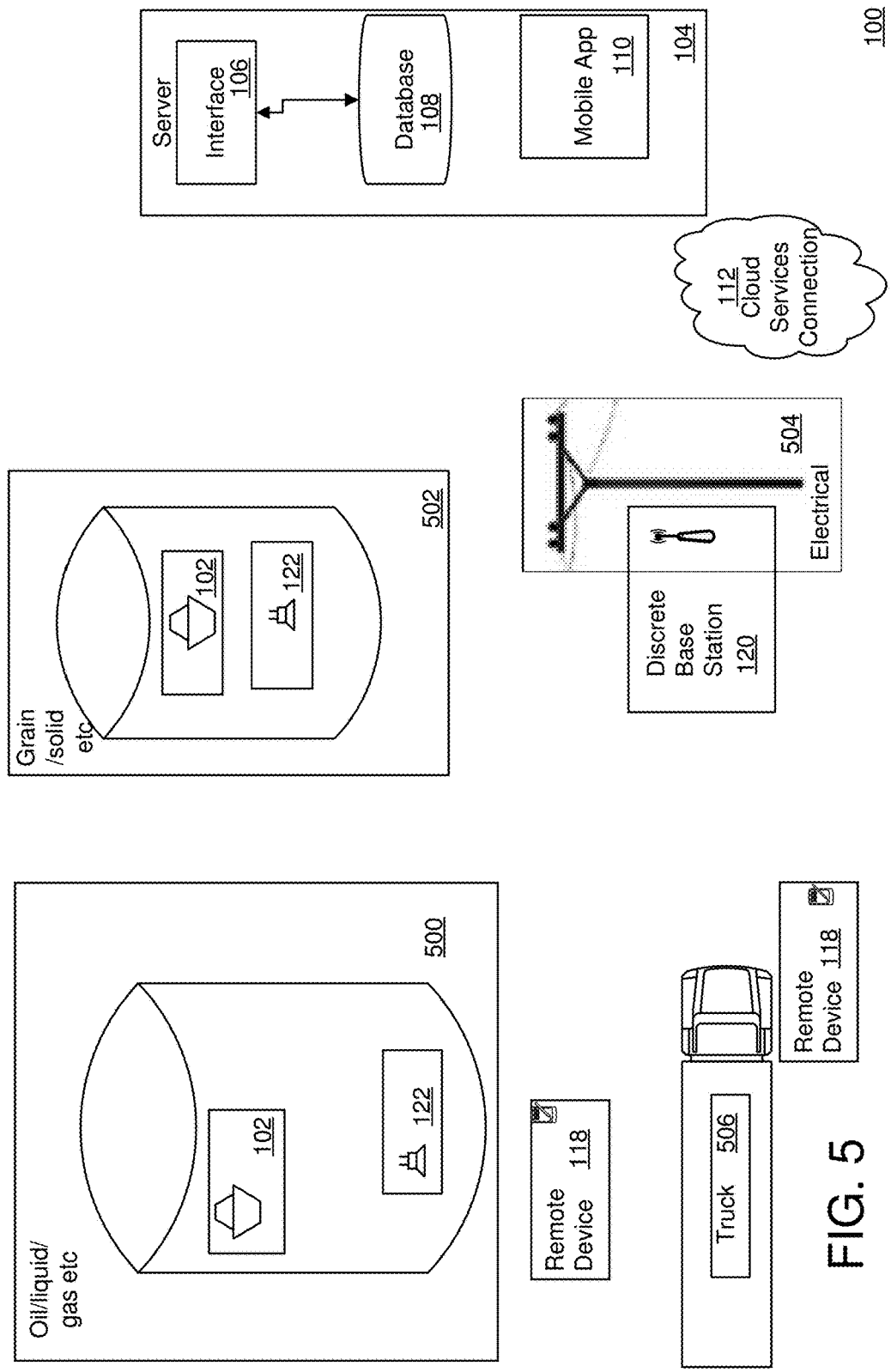

FIG. 5 is a real-world application of the system and method of FIGS. 1-4, for example, as applied to an oil or grain industry, and the like. In FIG. 5, the scenario illustrates the use of the disclosed digital network communication system and devices employed in a secure and encrypted manner for measurement, device reporting, and locking/unlocking devices, and the like, for alerting, reporting, statistical purposes, and the like, using quantifiable safety, security measures, and the like. For example, elements 500 and 502 are suitable containers, wherein the measuring device 102 is placed and employed for measurement of liquids or solids, and the like, inside the containers 500 or 502 (e.g., a tank, silo, etc.) in efficient, and potentially life-saving way, while using a low-powered source (e.g., battery power, etc.). The measuring device 102 communicates relevant information from the containers 500 or 502 to the base station device 120, which is placed discretely on/in electrical power area 504 (e.g., wired power, solar power, etc.) to receive power therefrom. The base station device 120 then communicates the received information via the communication network 112 to an authorized communication serve 104. The network communication server 104 then communicates pertinent information to the customer devices 118 for system convertible data to/for customer use. In conjunction with liquid or solid measurement 102, the locking mechanism 122 allows for system users to release and unlock the containers 500 or 502, allowing the liquid or material to be loaded onto a truck 506 or storage units, and the like. After the locking mechanism 122 is securely relocked, data is sent in an encrypted fashion, for example, using the near field device reader of the locking mechanism 122, and specifically allowed through authentication, personal identification methods, and the like, to ensure safe and authorized access to the containers, tanks, silos, and the like, 500 or 502. Upon successful transmission to the server 104, suitable algorithms and conversions can be configured to provide level, session, and the like, data to the customer, for example, including reports, alerts, warning messages, and the like. Authorized server operators can ensure that functionality is maintained and automation of data is properly converted for handling customer production, spills, leakage and other pertinent statistics, facts, figures, numbers, and the like, for customer usage, responsive actions, and the like.

Thus, the present invention provides a novel system and method for protecting and securing liquids, gasses, various other materials, devices, and the like, in a less expensive way, including tracking, measuring and monitoring tools, and computer applications. Advantageously, information regarding customer volumes, quantities, status, other pertinent information, and the like, can be securely monitored and obtained. The received information can be made available on a per customer basis, for example, according to customer device, and with functions separated via methods and structures determined by customer requirements, and the like.

The above-described devices and subsystems of the illustrative embodiments can include, for example, any suitable servers, workstations, PCs, laptop computers, personal digital assistant (PDAs), Internet appliances, handheld devices, cellular telephones, wireless devices, other electronic devices, and the like, capable of performing the processes of the illustrative embodiments. The devices and subsystems of the illustrative embodiments can communicate with each other using any suitable protocol and can be implemented using one or more programmed computer systems or devices.

One or more interface mechanisms can be used with the illustrative embodiments, including, for example, Internet access, telecommunications in any suitable form (e.g., voice, modem, and the like), wireless communications media, and the like. For example, employed communications networks or links can include one or more wireless communications networks, cellular communications networks, cable communications networks, satellite communications networks, 3G, 4G, 5G, etc., Long-Term Evolution (LTE), communications networks, Public Switched Telephone Network (PSTNs), Packet Data Networks (PDNs), the Internet, intranets, WiMax Networks, a combination thereof, and the like.

It is to be understood that the devices and subsystems of the illustrative embodiments are for illustrative purposes, as many variations of the specific hardware and/or software used to implement the illustrative embodiments are possible, as will be appreciated by those skilled in the relevant art(s). For example, the functionality of one or more of the devices and subsystems of the illustrative embodiments can be implemented via one or more programmed computer systems or devices.

To implement such variations as well as other variations, a single computer system can be programmed to perform the special purpose functions of one or more of the devices and subsystems of the illustrative embodiments. On the other hand, two or more programmed computer systems or devices can be substituted for any one of the devices and subsystems of the illustrative embodiments. Accordingly, principles and advantages of distributed processing, such as redundancy, replication, and the like, also can be implemented, as desired, to increase the robustness and performance the devices and subsystems of the illustrative embodiments.

The devices and subsystems of the illustrative embodiments can store information relating to various processes described herein. This information can be stored in one or more memories, such as a hard disk, optical disk, magneto-optical disk, volatile or non-volatile memory, and the like, of the devices and subsystems of the illustrative embodiments. One or more databases of the devices and subsystems of the illustrative embodiments can store the information used to implement the illustrative embodiments of the present invention. The databases can be organized using data structures (e.g., records, tables, arrays, fields, graphs, trees, lists, and the like) included in one or more memories or storage devices listed herein. The processes described with respect to the illustrative embodiments can include appropriate data structures for storing data collected and/or generated by the processes of the devices and subsystems of the illustrative embodiments in one or more databases thereof.

All or a portion of the devices and subsystems of the illustrative embodiments can be conveniently implemented using one or more general purpose computer systems, microprocessors, digital signal processors, micro-controllers, application processors, domain specific processors, application specific signal processors, and the like, programmed according to the teachings of the illustrative embodiments of the present invention, as will be appreciated by those skilled in the computer and software arts. Appropriate software can be readily prepared by programmers of ordinary skill based on the teachings of the illustrative embodiments, as will be appreciated by those skilled in the software art. In addition, the devices and subsystems of the illustrative embodiments can be implemented by the preparation of application-specific integrated circuits or by interconnecting an appropriate network of conventional component circuits, as will be appreciated by those skilled in the electrical art(s). Thus, the illustrative embodiments are not limited to any specific combination of hardware circuitry and/or software.

Stored on any one or on a combination of computer readable media, the illustrative embodiments of the present invention can include software for controlling the devices and subsystems of the illustrative embodiments, for driving the devices and subsystems of the illustrative embodiments, for enabling the devices and subsystems of the illustrative embodiments to interact with a human user, and the like. Such software can include, but is not limited to, device drivers, firmware, operating systems, development tools, applications software, and the like. Such computer readable media further can include the computer program product of an embodiment of the present invention for performing all or a portion (if processing is distributed) of the processing performed in implementing the illustrative embodiments. Computer code devices of the illustrative embodiments of the present invention can include any suitable interpretable or executable code mechanism, including but not limited to scripts, interpretable programs, dynamic link libraries (DLLs), Java classes and applets, complete executable programs, Common Object Request Broker Architecture (CORBA) objects, and the like. Moreover, parts of the processing of the illustrative embodiments of the present invention can be distributed for better performance, reliability, cost, and the like.

As stated above, the devices and subsystems of the illustrative embodiments can include computer readable medium or memories for holding instructions programmed according to the teachings of the present invention and for holding data structures, tables, records, and/or other data described herein. Computer readable medium can include any suitable medium that participates in providing instructions to a processor for execution. Such a medium can take many forms, including but not limited to, non-volatile media, volatile media, transmission media, and the like. Non-volatile media can include, for example, optical or magnetic disks, magneto-optical disks, and the like. Volatile media can include dynamic memories, and the like. Transmission media can include coaxial cables, copper wire, fiber optics, and the like. Transmission media also can take the form of acoustic, optical, electromagnetic waves, and the like, such as those generated during radio frequency (RF) communications, infrared (IR) data communications, and the like. Common forms of computer-readable media can include, for example, a floppy disk, a flexible disk, hard disk, magnetic tape, any other suitable magnetic medium, a CD-ROM, CDRW, DVD, any other suitable optical medium, punch cards, paper tape, optical mark sheets, any other suitable physical medium with patterns of holes or other optically recognizable indicia, a RAM, a PROM, an EPROM, a FLASH-EPROM, any other suitable memory chip or cartridge, a carrier wave, or any other suitable medium from which a computer can read.

While the present invention has been described in connection with a number of illustrative embodiments and implementations, the present invention is not so limited, but rather covers various modifications and equivalent arrangements, which fall within the purview of the appended claims.

What is claimed is:

1. A system for providing safety and security of materials, the system comprising:
    an onsite measuring device configured to measure dispensed liquid, fluids, or materials from a container at a site thereof, and transmit measurement information;
    a base station device configured to receive the transmitted measurement information from the onsite measuring device, and transmit the received measurement information over a communications network;
    a server device coupled to the base station device over the communications network, and configured to receive and process the measurement information, and transmit an authorization over the communications network to dispense the liquid, fluids, or materials in the container based on the processed measurement information;
    a mobile device configured to receive the authorization from the server device over the communications network to lock or unlock the container so as to dispense the liquid, fluids, or materials in the container; and
    a locking device configured to lock or unlock the container to dispense the liquid, fluids, or materials in the container based on the authorization received by the mobile device.

2. The system of claim 1, wherein the locking device is configured to lock or unlock the container to dispense the liquid, fluids, or materials in the container based on near field data (NFD) encryption communications with the mobile device, and the authorization received by the mobile device.

3. The system of claim 1, wherein the server is configured to generate for display logistical information based on the received and processed measurement information, including hierarchical event monitoring and analysis within an enterprise network including deploying a plurality of network monitors in the enterprise network.

4. The system of claim 1, wherein the onsite measuring device is configured to measure the liquid, fluids, or materials in the container based on volume inside the container for providing a digital representation or display thereof.

5. The system of claim 1, wherein the locking device is configured to employ an encryption based locking and unlocking mechanism for tracking, and securing the liquid, fluids, or materials in the container, and for providing corresponding information to the server.

6. The system of claim 1, wherein the server device is configured to send and receive information regarding measurements, locking and unlocking detection during collection and movement of the liquid, fluids, or materials in the container, and provide the received information to a computer system of an end-user customer.

7. A method for providing safety and security of materials, the method comprising:
   measuring with an onsite measuring device dispensed liquid, fluids, or materials from a container at a site thereof, and transmit measurement information;
   receiving with a base station device the transmitted measurement information from the onsite measuring device, and transmitting with the base station device the received measurement information over a communications network;
   receiving and processing with a server device coupled to the base station device over the communications network, the measurement information, and transmitting with the server device an authorization over the communications network to dispense the liquid, fluids, or materials in the container based on the processed measurement information;
   receiving with a mobile device the authorization from the server device over the communications network to lock or unlock the container so as to dispense the liquid, fluids, or materials in the container; and
   locking or unlocking with a locking device the container to dispense the liquid, fluids, or materials in the container based on the authorization received by the mobile device.

8. The method of claim 7, further comprising:
   locking or unlocking the container with the locking device to dispense the liquid, fluids, or materials in the container based on near field data (NFD) encryption communications with the mobile device, and the authorization received by the mobile device.

9. The method of claim 7, further comprising:
   generating for display with the server logistical information based on the received and processed measurement information, including hierarchical event monitoring and analysis within an enterprise network including deploying a plurality of network monitors in the enterprise network.

10. The method of claim 7, further comprising:
    measuring with the onsite measuring device the liquid, fluids, or materials in the container based on volume inside the container for providing a digital representation or display thereof.

11. The method of claim 7, further comprising:
    employing with the locking an encryption based locking and unlocking mechanism for tracking, and securing the liquid, fluids, or materials in the container, and for providing corresponding information to the server.

12. The method of claim 7, further comprising:
    sending and receiving with the server device information regarding measurements, locking and unlocking detection during collection and movement of the liquid, fluids, or materials in the container, and providing the received information to a computer system of an end-user customer.

13. A computer program product for providing safety and security of materials, and including one or more computer readable instructions embedded on a non-transitory, tangible computer readable medium and configured to cause one or more computer processors to perform the steps of:
    measuring with an onsite measuring device dispensed liquid, fluids, or materials from a container at a site thereof, and transmit measurement information;
    receiving with a base station device the transmitted measurement information from the onsite measuring device, and transmitting with the base station device the received measurement information over a communications network;
    receiving and processing with a server device coupled to the base station device over the communications network, the measurement information, and transmitting with the server device an authorization over the communications network to dispense the liquid, fluids, or materials in the container based on the processed measurement information;
    receiving with a mobile device the authorization from the server device over the communications network to lock or unlock the container so as to dispense the liquid, fluids, or materials in the container; and
    locking or unlocking with a locking device the container to dispense the liquid, fluids, or materials in the container based on the authorization received by the mobile device.

14. The computer program product of claim 13, further comprising:
    locking or unlocking the container with the locking device to dispense the liquid, fluids, or materials in the container based on near field data (NFD) encryption communications with the mobile device, and the authorization received by the mobile device.

15. The computer program product of claim 13, further comprising:
    generating for display with the server logistical information based on the received and processed measurement information, including hierarchical event monitoring and analysis within an enterprise network including deploying a plurality of network monitors in the enterprise network.

16. The computer program product of claim 13, further comprising:
    measuring with the onsite measuring device the liquid, fluids, or materials in the container based on volume inside the container for providing a digital representation or display thereof.

17. The computer program product of claim 13, further comprising:
    employing with the locking an encryption based locking and unlocking mechanism for tracking, and securing the liquid, fluids, or materials in the container, and for providing corresponding information to the server.

18. The computer program product of claim 13, further comprising:
    sending and receiving with the server device information regarding measurements, locking and unlocking detection during collection and movement of the liquid, fluids, or materials in the container, and providing the received information to a computer system of an end-user customer.

* * * * *